US009828620B2

(12) United States Patent
Liu et al.

(10) Patent No.: US 9,828,620 B2
(45) Date of Patent: *Nov. 28, 2017

(54) POROUS POLYMERIC FORMULATION PREPARED USING MONOMER

(71) Applicant: Verily Life Sciences LLC, Mountain View, CA (US)

(72) Inventors: Zenghe Liu, Mountain View, CA (US); Jeffrey George Linhardt, Mountain View, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 754 days.

This patent is subject to a terminal disclaimer.

(21) Appl. No.: 13/930,858

(22) Filed: Jun. 28, 2013

(65) Prior Publication Data

US 2015/0001073 A1    Jan. 1, 2015

(51) Int. Cl.
C12Q 1/00    (2006.01)
G01N 27/327    (2006.01)

(52) U.S. Cl.
CPC .................................. C12Q 1/003 (2013.01)

(58) Field of Classification Search
CPC ............. G01N 27/3274; G01N 27/327; G01N 27/3272; A61L 2/206; A61B 5/14532; A61B 5/14546; A61B 5/1486
See application file for complete search history.

(56) References Cited

U.S. PATENT DOCUMENTS

| 4,889,689 A * | 12/1989 | Tsao ........................ A01N 59/00 252/186.28 |
| 4,929,313 A | 5/1990 | Wrighton |
| 5,543,326 A | 8/1996 | Heller et al. |
| 5,683,563 A | 11/1997 | Mizutani et al. |
| 5,928,918 A | 7/1999 | Offenbacher |
| 6,653,358 B2 | 11/2003 | Bruza |
| 6,654,625 B1 | 11/2003 | Say et al. |
| 6,927,246 B2 | 8/2005 | Noronha |
| 7,731,826 B2 | 6/2010 | Buck |
| 8,088,595 B2 | 1/2012 | Ibey |
| 8,224,414 B2 | 7/2012 | Kellogg |
| 8,241,819 B2 | 8/2012 | Lowe |
| 8,385,998 B2 | 2/2013 | Zhang |
| 8,437,829 B2 | 5/2013 | Mao |
| 2007/0114138 A1 | 5/2007 | Krasteva et al. |
| 2009/0280181 A1 | 11/2009 | Slager |
| 2010/0175992 A1 | 7/2010 | Shah |
| 2010/0279377 A1 | 11/2010 | Shah |
| 2010/0280347 A1 | 11/2010 | Shah |
| 2010/0300897 A1 | 12/2010 | Savage |
| 2011/0082356 A1 | 4/2011 | Yang et al. |
| 2011/0136929 A1* | 6/2011 | Chow ................. A61B 5/14532 521/105 |
| 2011/0152654 A1 | 6/2011 | Wang |
| 2012/0116191 A1 | 5/2012 | Markle |
| 2012/0186997 A1 | 7/2012 | Xiaolong |
| 2012/0245444 A1 | 9/2012 | Otis |
| 2012/0283537 A1 | 11/2012 | Petisce |
| 2012/0296186 A1 | 11/2012 | Ouyang et al. |
| 2013/0011460 A1 | 1/2013 | Liu |
| 2013/0084649 A1 | 4/2013 | Crane |

FOREIGN PATENT DOCUMENTS

| EP | 1927602 | 6/2008 |
| WO | 2002097414 | 12/2002 |
| WO | 2003098165 | 11/2003 |
| WO | 2006050115 A1 | 5/2006 |
| WO | 2007137037 | 11/2007 |
| WO | 2011084651 A1 | 7/2011 |
| WO | 2012161735 | 11/2012 |

OTHER PUBLICATIONS

PEGMA—Specification from Sigma Aldrich.*
International Search Report issued in connection with co-pending International Patent Application No. PCT/US2014/044609, ISA/KR dated Oct. 14, 2014, 6 pgs.
Written Opinion issued in connection with co-pending International Patent Application No. PCT/US2014/044609, ISA/KR dated Oct. 14, 2014, 5 pgs.
Gil, M.H., et al., "Immobilization of Glucose Oxidase on Thin-Film Gold Electrodes Produced by Magnetron Sputtering and Their Application in an Electrochemical Biosensor," Biotechnology Techniques, vol. 13, pp. 595-599 (1999).
Hall, C.E. et al., "Covalent Immobilisation of Glucose Oxidase on Methacrylate Copolymers for Use in an Amperometric Glucose Sensor," Analytica Chimica Acta, vol. 281, pp. 645-653 (1993).
Jusoh, Norhana et al., "Improvement of Glucose Biosensor Performances Using Poly(hydroxyethylmethacrylate) Outer Membrane," International Journal of Biology and Biomedical Engineering, Issue 1, vol. 6, pp. 77-86 (2012).
Slaughter, Gymama Ph.D., "Fabrication of Nanoindented Electrodes for Glucose Detection," Journal of Diabetes Science and Technology, vol. 4, Issue 2, pp. 320-327 (Mar. 2010).

(Continued)

Primary Examiner — Gurpreet Kaur
(74) Attorney, Agent, or Firm — McDonnell Boehnen Hulbert & Berghoff LLP

(57) ABSTRACT

An analyte sensor for the continuous or semi-continuous monitoring of physiological parameters and a method for making the analyte sensor are disclosed. In one aspect, the analyte sensor includes a crosslinked, hydrophilic copolymer in contact with a surface of an electrode, and an analyte sensing component embedded within the crosslinked, hydrophilic copolymer. The crosslinked, hydrophilic copolymer has methacrylate-derived backbone chains of first methacrylate-derived units, second methacrylate-derived units and third methacrylate-derived units. The first and second methacrylate-derived units have side chains that can be the same or different, and the third methacrylate-derived units in different backbone chains are connected by hydrophilic crosslinks.

12 Claims, 1 Drawing Sheet

(56) References Cited

OTHER PUBLICATIONS

Akkaya, et al., "Functional polymer supports for immobilization of cholesterol oxidase", Biochemical Engineering Journal, vol. 43, No. 3, Mar. 2009, p. 333-337.
European Search Report issued in connection with co-pending European Patent Application No. 14817262.0, search performed Jan. 17, 2017, dated Jan. 25, 2017, pp. 1-10.
Tohda, K. et al. "Modelling the response function of enzyme-based optical glucose-sensing capsules" 2010, Supra molecular Chemistry, 22:7-8, p. 425-433.
Wang, C. et al. "Synthesis and Performance of Novel Hydrogels Coatings for Implantable Glucose Sensors" 2008, Biomacromolecules, 9, p. 561-567.
Perez, J. P. H. et al. "The application of methacrylate-based polymers to enzyme biosensors" 2006, Biomolecular, Engineering 23, p. 233-245.
Boztas, A. O. et al. "Immobilization and Release of the Redox Mediator Ferrocene Monocarboxylic Acid from within Cross-Linked p(HEMA-co-PEGMA-co-HMMA) Hydrogels" 2009, Biomacromolecules, 10, p. 2135-2143.
Paeng, K. et al "Molecular mobility in supported thin films of polystyrene, poly(methyl methacrylate), and poly(2-vinylpyridine) probed by dye reorientation" Soft Matter, 2012, 8, 819-826.

\* cited by examiner

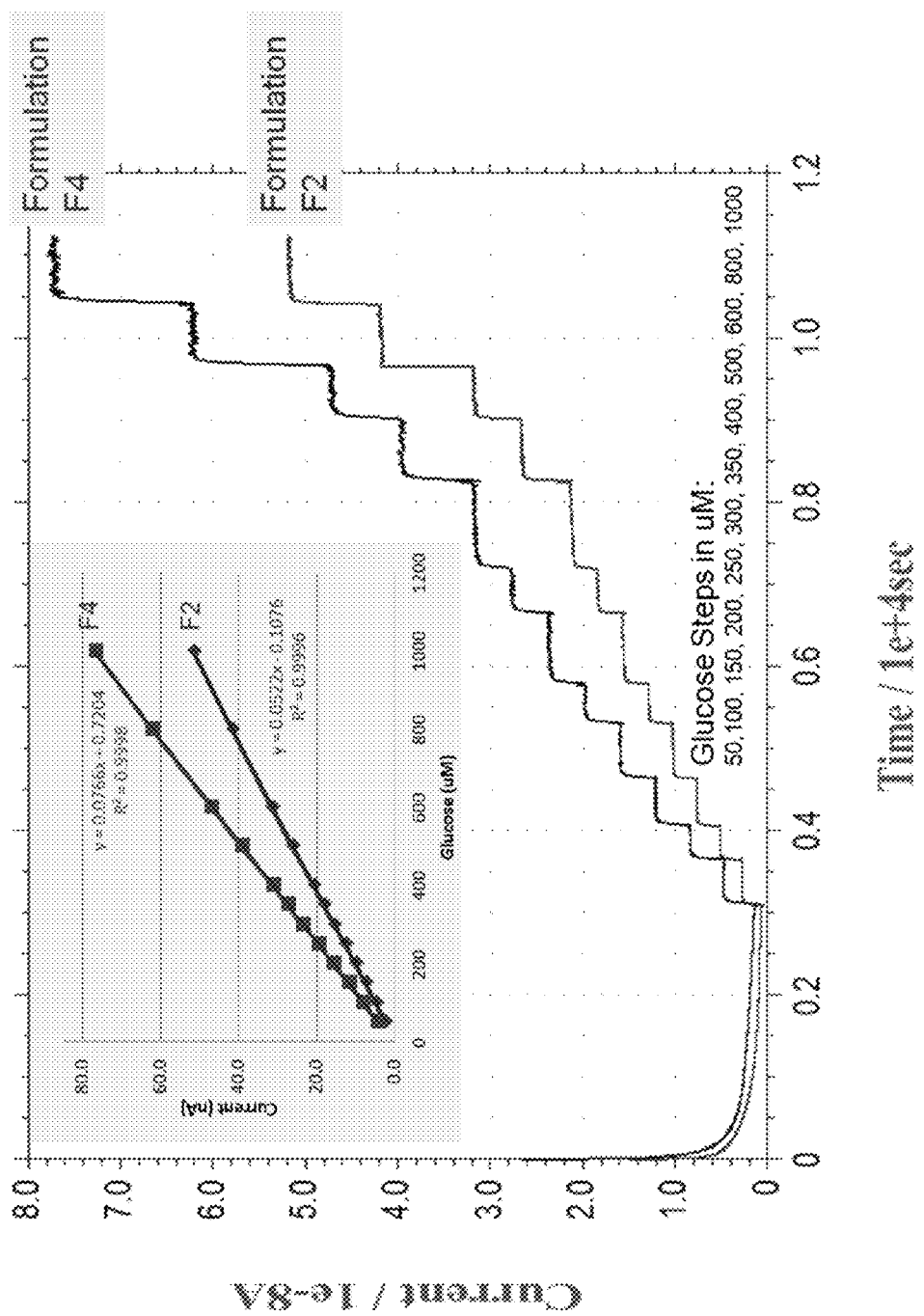

POROUS POLYMERIC FORMULATION PREPARED USING MONOMER

BACKGROUND

Unless otherwise indicated herein, the materials described in this section are not prior art to the claims in this application and are not admitted to be prior art by inclusion in this section.

The continuous or semi-continuous monitoring of physiological parameters has applications in many areas of modern medicine. Electrochemical-based sensors are believed to be particularly suitable for the monitoring and quantification of analytes (e.g., glucose) in bodily fluid samples (e.g., blood, tear film, urine or interstitial fluid samples). The use of an electrochemical-based sensor that employs an analyte sensing component, (e.g., an enzyme) in conjunction with an electrode(s) allows for the quantification of an analyte in a liquid sample by detecting the product(s) produced from the reaction of the analyte sensing component and the analyte.

SUMMARY

In one aspect, an analyte sensor is disclosed. The analyte sensor includes a crosslinked, hydrophilic copolymer in contact with a surface of an electrode, and an analyte sensing component embedded within the crosslinked, hydrophilic copolymer. The crosslinked, hydrophilic copolymer has methacrylate-derived backbone chains of first methacrylate-derived units, second methacrylate-derived units and third methacrylate-derived units. The first and second methacrylate-derived units have side chains that can be the same or different, and the third methacrylate-derived units in different backbone chains are connected by hydrophilic crosslinks.

In another aspect, a method for forming an analyte sensor is disclosed. The method involves forming mixture including the precursor components of the sensor, depositing the mixture onto a surface of an electrode, and curing the deposited mixture. The mixture includes an analyte sensing component, a first methacrylate monomer having a first hydrophilic side chain, a dimethacrylate monomer, an initiator, and a second methacrylate monomer having a second hydrophilic side chain.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 1 is a graph of current produced by two example glucose sensors at glucose concentrations of 20 µM to 1,000 µM in phosphate buffered saline (PBS). A linear relationship between current and glucose concentration was observed (see inset graph).

DETAILED DESCRIPTION

The following detailed description describes various features and functions of the disclosed systems and methods with reference to the accompanying figures. In the figures, similar symbols typically identify similar components, unless context dictates otherwise. The illustrative method and system embodiments described herein are not meant to be limiting. It will be readily understood that certain aspects of the disclosed methods and systems can be arranged and combined in a wide variety of different configurations, all of which are contemplated herein.

In one aspect, an analyte sensor is disclosed. The analyte sensor includes: a crosslinked, hydrophilic copolymer in contact with a surface of an electrode; and an analyte sensing component embedded within the crosslinked, hydrophilic copolymer, where the crosslinked, hydrophilic copolymer includes:
  backbone chains having
  first methacrylate-derived units, each having a first hydrophilic side chain;
  second methacrylate-derived units, each having a second hydrophilic side chain, where the first and second side chains are the same or different;
  third methacrylate-derived units; and
  hydrophilic crosslinks between third methacrylate-derived units in different backbone chains.

In some embodiments, the analyte sensor is an enzyme-based biosensor. These devices are able to convert an analyte-concentration-dependent biochemical reaction signal into a measurable physical signal, such as an optical or electrical signal. The biosensors can be used in the detection of analytes in clinical, environmental, agricultural and biotechnological applications. Analytes that can be measured in clinical assays of fluids of the human body include, for example, glucose, lactate, cholesterol, bilirubin, proteins, lipids and electrolytes. The detection of analytes in biological fluids, such as blood, tear film, or intestinal fluid, can be important in the diagnosis and the monitoring of many diseases.

In some embodiments, the analyte sensor can be a component of a body-mountable device, such as an eye-mountable, tooth-mountable, or skin-mountable device. The eye-mountable device can be configured to monitor health-related information based on one or more analytes detected in a tear film (the term "tear film" is used herein interchangeably with "tears" and "tear fluid") of a user wearing the eye-mountable device. For example, the eye-mountable device can be in the form of a contact lens that includes a sensor configured to detect one or more analytes (e.g., glucose). The eye-mountable device can also be configured to monitor various other types of health-related information.

In some embodiments, the body-mountable device may comprise a tooth-mountable device. The tooth-mountable device may take the form of or be similar in form to the eye-mountable device, and be configured to detect at least one analyte in a fluid (e.g., saliva) of a user wearing the tooth-mountable device.

In some embodiments, the body-mountable device may comprise a skin-mountable device. The skin-mountable device may take the form of or be similar in form to the eye-mountable device, and be configured to detect at least one analyte in a fluid (e.g., perspiration, blood, etc.) of a user wearing the skin-mountable device.

The sensor as described herein can include one or more conductive electrodes through which current can flow. Depending on the application, the electrodes can be configured for different purposes. For example, a sensor can include a working electrode, a reference electrode, and a counter-electrode. Also possible are two-electrode systems, in which the reference electrode serves as a counter-electrode. The working electrode can be connected to the reference electrode via a circuit, such as a potentiostat.

The electrode can be formed from any type of conductive material and can be patterned by any process that be used for patterning such materials, such as deposition or photolithography, for example. The conductive materials can be, for example, gold, platinum, palladium, titanium, carbon, copper, silver/silver-chloride, conductors formed from noble materials, metals, or any combinations of these materials. Other materials can also be envisioned.

The crosslinked, hydrophilic copolymer of the analyte sensor includes backbone chains of methacrylate-derived units, and an analyte sensing component, such as an enzyme, embedded within the copolymer. Each of the first and second methacrylate-derived units of the backbones are covalently bound independently to first and second hydrophilic side chains, respectively. Each of the third methacrylate-derived units is covalently bound through a linker to another third methacrylate-derived unit in a different backbone chain. The crosslinks, or groups through which the third methacrylate-derived units are connected, are discussed in greater detail below. Various conformations and compositions of the side chains of the first and second methacrylate-derived units, and the crosslinks of the third methacrylate-derived units can be used to adjust the properties of the crosslinked, hydrophilic copolymer as desired, which include hydrophilicity, permeability and the ability to immobilize an analyte sensing component.

The side chains of the first and second methacrylate-derived units are hydrophilic, and can be water soluble or soluble in a water-miscible solvent, such as an alcohol. The side chains can have one or more heteroatoms, for example, nitrogen, oxygen or sulfur atoms. In some embodiments, the side chains have one or more hydroxy groups.

In some embodiments, the side chains of the first and second methacrylate-derived units include one or more alkylene oxide units. The alkylene oxide units can be in the form of a polymer, such as poly(ethylene glycol), poly(propylene glycol), poly(butylene oxide) or a mixture thereof, and can be a copolymer including a combination of two or three different alkylene oxide units. In some embodiments, the poly(alkylene oxide) of the side chains is a block copolymer including blocks of two or three different poly(alkylene oxide) polymers. In certain embodiments, the poly(alkylene oxide) is block copolymer of poly(ethylene glycol) and poly(propylene glycol). In other embodiments, the second side chain and the crosslinks both include poly(ethylene glycol).

In some embodiments, the first methacrylate-derived units can have the structure of formula (I):

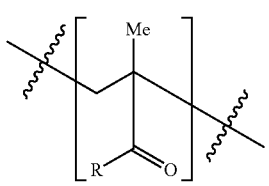

where R is a hydrophilic group. In certain embodiments, the hydrophilic group includes one or more hydroxy groups, such as an alcohol.

In some embodiments, the first methacrylate-derived units can have the structure of formula (Ia):

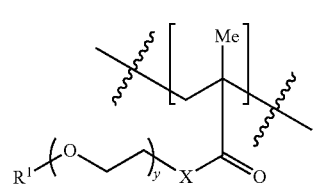

where X is —O—, —NR'— or —S—, y is 0, 1, 2, 3, 4, 5, 6, 7, 8, 9 or 10, and $R^1$ is hydrogen, —$C_1$-$C_{12}$alkyl, —$C_1$-$C_{12}$alkyl-OH, —SiR'$_3$, —C(O)—$C_1$-$C_{12}$alkyl, —$C_1$-$C_{12}$alkyl-C(O)OR', where R' is —$C_1$-$C_{12}$alkyl.

In certain embodiments, the first methacrylate-derived units have the structure:

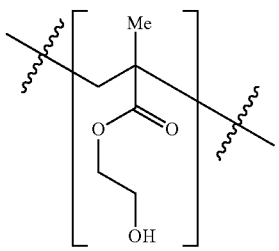

In some embodiments, the second methacrylate-derived units can have the structure of formula (II):

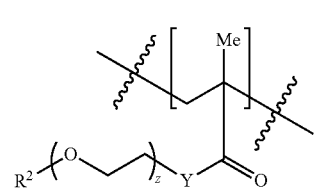

where Y is —O—, —NR'— or —S—, z is 0, 1, 2, 3, 4, 5, 6, 7, 8, 9 or 10, and $R^2$ is hydrogen, —$C_1$-$C_{12}$alkyl, —SiR'$_3$, —C(O)—$C_1$-$C_{12}$alkyl, —$C_1$-$C_{12}$alkyl-C(O)OR', where R' is hydrogen or —$C_1$-$C_{12}$alkyl.

In certain embodiments, z is an average value of from about 2 to about 250.

In some embodiments, the second methacrylate-derived units can have the structure of formula (IIa):

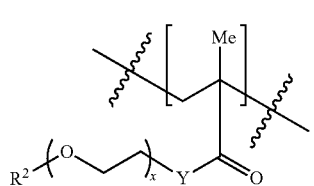

where Y and $R^2$ are as described above and x is such that the poly(ethylene glycol) has a number average molecular weight ($M_n$) of about 100 to about 10,000. In certain embodiments, x is selected so that the $M_n$ of the poly(ethylene glycol) falls within a range in Table 1.

TABLE 1

Mₙ range of poly(ethylene glycol) in the second
methacrylate-derived units (values are approximate).

| Low | High |
|---|---|
| 100 | 200 |
| 200 | 300 |
| 300 | 400 |
| 400 | 500 |
| 500 | 600 |
| 600 | 700 |
| 700 | 800 |
| 800 | 900 |
| 900 | 1,000 |
| 1,000 | 2,000 |
| 2,000 | 3,000 |
| 3,000 | 4,000 |
| 4,000 | 5,000 |
| 5,000 | 6,000 |
| 7,000 | 8,000 |
| 8,000 | 9,000 |
| 9,000 | 10,000 |

In certain embodiments, the analyte sensor has second methacrylate-derived units having the structure of formula (IIa), where Y is —O—, $R^2$ is methyl and x is such that the poly(ethylene glycol) has a number average molecular weight ($M_n$) of about 500.

In some embodiments, the presence of the second methacrylate-derived units having second hydrophilic side chains in the crosslinked, hydrophilic copolymer of the analyte sensor can form a porous network. The structure of the porous network includes regions within the copolymer that are not occupied by polymer, these regions are referred to herein as "pores". The porous network of the crosslinked, hydrophilic copolymer can facilitate control of the equilibrium between the concentration of the analyte (e.g., glucose) in the sample solution, and the analyte concentration in the proximity of the analyte sensor electrode surface. When all of the analyte arriving at the analyte sensor is consumed, the measured output signal can linearly proportional to the flow of the analyte and thus to the concentration of the analyte. However, when the analyte consumption is limited by the kinetics of chemical or electrochemical activities in the analyte sensor, the measured output signal may no longer be controlled by the flow of analyte and is no longer linearly proportional to the flow or concentration of the analyte. In this case, only a fraction of the analyte arriving at the analyte sensing component is consumed before the sensor becomes saturated, whereupon the measured signal stops increasing, or increases only slightly, with an increasing concentration of the analyte. The porous network can reduce the flow of the analyte to the analyte sensing component so the sensor does not become saturated and can therefore effectively enable a wider range of analyte concentrations to be measured.

The hydrophilic properties of the second side chain of the second methacrylate-derived units can be varied to produce desired properties of the porous network, such as permeability of the analyte. For example, flow of the analyte into or across the sensor can be dependent on the specific analyte being monitored, and thus, the porous network can be altered to obtain properties for monitoring a specific analyte. In some applications, the hydrophilicity of the porous network can be adjusted by changing the number alkylene oxide units in the second side chain. Similarly, the hydrophilicity of the porous network can be adjusted by modifying the ratio of carbon atoms (i.e., —C—, —CH—, —CH$_2$— or —CH$_3$) to alkylene oxide units in the second methacrylate-derived units.

The analyte sensing component is embedded, i.e., surrounded by the polymer network of the crosslinked, hydrophilic copolymer The embedded analyte sensing component is immobilized and can interact with a corresponding analyte of interest. In some embodiments, the analyte sensing component includes an enzyme.

The analyte sensing component of the analyte sensor can be selected to monitor physiological levels of a specific analyte. For example, glucose, lactate, cholesterol and various proteins and lipids can be found in body fluids, including, for example, tear film, and can be indicative of medical conditions that can benefit from continuous or semi-continuous monitoring.

The analyte sensing component can be an enzyme selected to monitor one or more analytes. For example, physiological cholesterol levels can be monitored with cholesterol oxidase, lactate levels with lactate oxidase, and glucose levels with glucose oxidase or glucose dehydrogenase (GDH).

In some embodiments, the analyte sensing component can be an enzyme that undergoes a chemical reaction with an analyte to produce detectable reaction products. For example, a copolymer including glucose oxidase ("GOx") can be situated around the working electrode to catalyze a reaction with glucose to produce hydrogen peroxide ($H_2O_2$). As shown below, the hydrogen peroxide can then be oxidized at the working electrode to releases electrons to the working electrode, which generates a current.

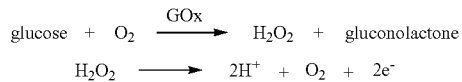

$$\text{glucose} + O_2 \xrightarrow{\text{GOx}} H_2O_2 + \text{gluconolactone}$$
$$H_2O_2 \longrightarrow 2H^+ + O_2 + 2e^-$$

The current generated by either reduction or oxidation reactions can be approximately proportionate to the reaction rate. Further, the reaction rate can be dependent on the rate of analyte molecules reaching the electrochemical sensor electrodes to fuel the reduction or oxidation reactions, either directly or catalytically through a reagent. In a steady state, where analyte molecules diffuse to the electrochemical sensor electrodes from a sampled region at approximately the same rate that additional analyte molecules diffuse to the sampled region from surrounding regions, the reaction rate can be approximately proportionate to the concentration of the analyte molecules. The current can thus provide an indication of the analyte concentration.

In other embodiments, the analyte sensing component is glucose dehydrogenase (GDH). In certain instances, the use of GDH can require the addition of a cofactor such as flavin adenine dinucleotide (FAD), nicotinamide adenine dinucleotide (NAD), flavin mononucleotide, pyrroloquinoline quinone (PQQ) or a coenzyme.

The crosslinks of the crosslinked, hydrophilic copolymer connect the third methacrylate-derived units in different backbone chains, and are represented by "A" in formula (III):

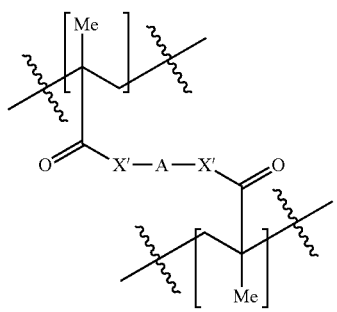

(III)

where X' is independently —O—, —NR'— or —S—, and A is a hydrophilic group.

In some embodiments, the crosslinks are hydrophilic. The crosslinks can be soluble in water or a water-miscible solvent, such as an alcohol. The crosslinks can have one or more heteroatoms, for example, nitrogen, oxygen or sulfur atoms. In some embodiments, the crosslinks have one or more hydroxy groups.

In some embodiments, the crosslinks include one or more alkylene oxide units. The alkylene oxide units can be in the form of a polymer, such as poly(ethylene glycol), poly(propylene glycol), poly(butylene oxide) or a mixture thereof, and can be a copolymer including a combination of two or three different alkylene oxide units. In some embodiments, the poly(alkylene oxide) of the crosslinks is a block copolymer including blocks of two or three different poly(alkylene oxide) polymers. In certain embodiments, the poly(alkylene oxide) is a block copolymer of poly(ethylene glycol) and poly(propylene glycol). In other embodiments, the crosslinks and the second methacrylate-derived units include poly(ethylene glycol).

In some embodiments, the crosslinks include one or more ethylene oxide units. For example, the crosslinks (e.g., A in formula (III) above) can have the structure of formula (IIIa):

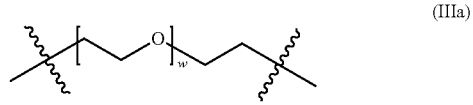

(IIIa)

where w is 0, 1, 2, 3, 4, 5, 6, 7, 8, 9 or 10.

In certain embodiments, w is an average value of from about 2 to about 250.

In other embodiments, w in the crosslinks of formula (IIIa) is such that the number average molecular weight ($M_n$) of the PEG portion (within the brackets in formula (IIIa)) of the crosslinks is about 100 to about 10,000. For example, w can be selected such that the $M_n$ of the PEG portion of the crosslinks falls within a range in Table 2:

TABLE 2

| $M_n$ range of the PEG portion of the crosslinks (values are approximate). | |
|---|---|
| Low | High |
| 100 | 200 |
| 200 | 300 |
| 300 | 400 |
| 400 | 500 |

TABLE 2-continued

| $M_n$ range of the PEG portion of the crosslinks (values are approximate). | |
|---|---|
| Low | High |
| 500 | 600 |
| 600 | 700 |
| 700 | 800 |
| 800 | 900 |
| 900 | 1,000 |
| 1,000 | 2,000 |
| 2,000 | 3,000 |
| 3,000 | 4,000 |
| 4,000 | 5,000 |
| 5,000 | 6,000 |
| 7,000 | 8,000 |
| 8,000 | 9,000 |
| 9,000 | 10,000 |

In some embodiments, the crosslinks are derived from di(ethylene glycol) dimethacrylate, where w is 1.

The thickness of the crosslinked, hydrophilic copolymer of the analyte sensor can vary depending on the desired properties of the analyte sensor. The thickness of the copolymer, as measured from the top of electrode to the top of the copolymer, can play an important role in regulating the flow of the analyte to the analyte sensing component. Depending on the characteristics of the methacrylate-derived units in the copolymer the type of analyte sensing component used, and the analyte to be monitored, the thickness of the copolymer can be from less than about 10 μm to about 30 μm. In some instances, the copolymer is less than 20 μm in thickness, where in other applications the copolymer is about 20 μm to about 25 μm in thickness. In certain applications, the copolymer is about 10 μm to about 15 μm in thickness, where in other applications the copolymer is about 15 μm to about 20 μm or about 25 μm to about 30 μm in thickness. In some embodiments, the copolymer is about 20 μm in thickness.

In another aspect, a method for making an analyte sensor is disclosed. The method can involve:

a) forming a mixture including an analyte sensing component, a dimethacrylate monomer, an initiator, a first methacrylate monomer having a first hydrophilic side chain, and a second methacrylate monomer having a second hydrophilic side chain;

b) depositing the mixture onto a surface of an electrode; and c) subjecting the deposited mixture to conditions sufficient to initiate polymerization (i.e., curing).

In some embodiments of the method, the mixture is formed by combining three separate solutions. The method can involve:

a) forming a first solution which includes an analyte sensing component;

b) forming a second solution which includes a dimethacrylate monomer, an initiator, and a first methacrylate monomer having a first hydrophilic side chain;

c) forming a third solution which includes a dimethacrylate monomer, an initiator, and a second methacrylate monomer having a second hydrophilic side chain;

d) combining the three solutions to provide the mixture.

In some embodiments, the mixture can be formed on a surface of an electrode. For example, each component, or a combination of one or more components, can be individually deposited to form the mixture. Similarly, when the mixture is formed by combining three separate solutions, the solutions can combined on a surface of an electrode to form the mixture.

The ratio of the sensor precursors in the mixture can vary depending on the desired properties of the resulting analyte sensor. For example, adjusting the amount of the second methacrylate monomer having a second hydrophilic side chain can alter the porous network of the crosslinked, hydrophilic copolymer. Controlling the properties of the porous network can allow for the tuning of the permeability of the analyte sensor. Similar tunability can also be accomplished by adjusting the amount of the mixture deposited on the electrode, and/or adjusting the amount of the second methacrylate monomer combined with the first methacrylate monomer.

The mixture, or the first, second and third solutions can be formed in an aqueous medium, alcoholic medium, or mixture thereof. The aqueous medium can include a buffered aqueous solution, such as, for example, a solution containing citric acid, acetic acid, borate, carbonate, bicarbonate, 4-2-hydroxyethyl-1-piperazineethanesulfonic acid (HEPES), 3-{[tris(hydroxymethyl)methyl]amino}propanesulfonic acid (TAPS), N,N-bis(2-hydroxyethyl)glycine (Bicine), tris (hydroxymethyl)methylamine (Tris), N-tris(hydroxymethyl) methylglycine (Tricine), 3-[N-Tris(hydroxymethyl)methyl-amino]-2-hydroxypropanesulfonic acid (TAPSO), 2-{[tris (hydroxymethyl)methyl]amino}ethanesulfonic acid (TES), 3-(N-morpholino)propanesulfonic acid (MOPS), piperazine-N,N'-bis(2-ethanesulfonic acid) (PIPES), dimethylarsinic acid (Cacodylate), saline sodium citrate (SSC), 2-(N-morpholino)ethanesulfonic acid (MES), 2(R)-2-(methylamino)succinic acid, or phosphate buffered saline (PBS). In some embodiments, the mixture, or first, second and third solutions can be formed in a mixture of a buffered aqueous solution and ethanol.

In some embodiments of the method, the first, second and third solutions of the method can be formed with approximately the same concentration of analyte sensing component, first methacrylate monomer, and second methacrylate monomer, respectively. The percentage of each component can then be varied by adjusting the amounts each solution used to form the mixture. In some instances, the percentage of analyte sensing component in the mixture, is about 20% by weight to about 50% by weight, the percentage of first methacrylate monomer is 20% by weight to about 60% by weight, and the percentage of second methacrylate monomer is about 10% by weight to about 40% by weight. All percentages are given as a percentage of the cumulative amount of analyte sensing component, first methacrylate monomer and second methacrylate monomer. In certain examples, the percentage of analyte sensing component is about 40%, the amount of first methacrylate monomer is about 35% to about 40%, and the amount of second methacrylate monomer is about 20% to about 25%. In certain embodiments, the mixture is thoroughly mixed, optionally with a stirrer or shaker, before being deposited onto a surface of an electrode.

The analyte sensing component can be selected based on the analyte desired to be monitored. For example, to monitor physiological cholesterol levels, cholesterol oxidase can be used, and to monitor lactate levels lactate oxidase can be used. To monitor glucose levels, the analyte sensing component can include glucose oxidase or glucose dehydrogenase (GDH).

The analyte sensing component can be present during polymerization of the methacrylate and dimethacrylate monomers in the deposited mixture, such that polymerization of the methacrylate and dimethacrylate monomers results in the formation of a crosslinked, copolymer network in which the analyte sensing component is embedded. The embedded analyte sensing component is immobilized and can be used to monitor a corresponding analyte of interest.

The first and second methacrylate monomers include hydrophilic side chains that can have one or more heteroatoms. The first and second side chains can include one or more alkylene oxide units to form the crosslinked, hydrophilic copolymer of the analyte sensor as described herein.

In some embodiments of the method, the first methacrylate monomer has the structure of formula (IV):

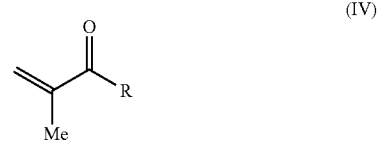

where R is a hydrophilic group. In certain embodiments of the method, the hydrophilic group includes one or more hydroxy groups, such as an alcohol.

In some embodiments of the method, the first methacrylate monomer has the structure of formula (IVa):

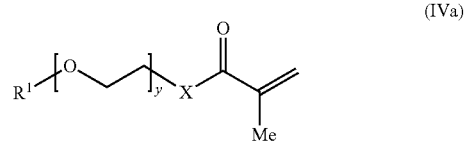

where X, y, $R^1$, and R' are selected to provide the first methacrylate-derived monomeric unit of the crosslinked, hydrophilic copolymer described herein.

In certain embodiments of the method, the first methacrylate monomer has the structure:

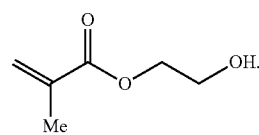

In some embodiments of the method, the second methacrylate monomer has the structure of formula (V):

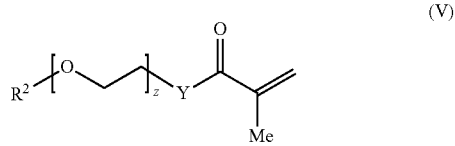

where Y, z, $R^2$ and R' are selected to provide the second methacrylate-derived monomeric unit of the crosslinked, hydrophilic copolymer described herein.

In some embodiments of the method, the second methacrylate monomer has the structure of formula (Va):

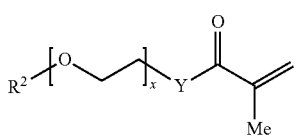

(Va)

where x is selected to provide second methacrylate-derived monomeric units of the crosslinked, hydrophilic copolymer described herein where the poly(ethylene glycol) has a number average molecular weight ($M_n$) of about 100 to about 10,000. In certain embodiments, x is selected to provide second methacrylate-derived monomeric units where the $M_n$ of the poly(ethylene glycol) falls within a range in Table 1.

In certain embodiments of the method, the second methacrylate monomer has the structure of formula (Va), where Y is —O—, $R^2$ is methyl and x is such that the poly(ethylene glycol) has a number average molecular weight ($M_n$) of about 500.

The dimethacrylate monomer is a molecule having two terminal methacrylate groups tethered by a hydrophilic linker. The hydrophilic linker is selected to provide the crosslinks between third methacrylate-derived units in different backbone chains of the crosslinked, hydrophilic copolymer described herein. In embodiments where the mixture is formed from the combination of two or more solutions each having a dimethacrylate monomer, the dimethacrylate monomers can be the same, or in some instances, can be different.

The extent of crosslinking in crosslinked, hydrophilic copolymer of the analyte sensor can be controlled by adjusting the amount of dimethacrylate monomer in the mixture. In some embodiments, the dimethacrylate monomer is about 1% to about 15% of the mixture. In other examples, the amount is about 1% to about 5%, or about 5% to about 10%, or about 10% to about 15%. In some embodiments, the amount is about 1%. In some instances, both the mixture includes about 1% of the dimethacrylate monomer.

In some embodiments of the method, the dimethacrylate monomer includes one or more alkylene oxide units to provide the crosslinks of the crosslinked, hydrophilic copolymer as described herein. In some embodiments, the dimethacrylate monomer includes poly(ethylene glycol) (PEG). For example, the dimethacrylate monomer can have the structure of formula (VI):

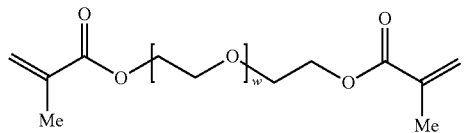

(VI)

where w is 0, 1, 2, 3, 4, 5, 6, 7, 8, 9 or 10.

In certain embodiments, w is an average value of from about 2 to about 250.

In other embodiments of the method, the dimethacrylate monomer can have the structure of formula (VI) where w is such that the number average molecular weight ($M_n$) of the PEG portion of the dimethacrylate monomer is about 100 to about 10,000. For example, w can be selected such that the $M_n$ of the PEG portion of the dimethacrylate monomer falls within a range in Table 2. In some embodiments, the dimethacrylate monomer is di(ethylene glycol) dimethacrylate.

Depositing the mixture onto a surface of an electrode can be accomplished by a number of methods. For example, the depositing can be performed manually with a micro-syringe, or by automated fabrication processes with nano jet dispensing equipment.

In some embodiments of the method, the amount of the mixture deposited onto a surface of an electrode is selected to provide the desired thickness of the crosslinked, hydrophilic copolymer of the analyte sensor. In some embodiments, the amount deposited on the electrode is about 50 mL/mm² to about 500 mL/mm². In other examples, the amount is about 50 μm to about 150 μm, or about 150 μm to about 300 μm, or about 300 μm to about 500 μm in thickness. In some embodiments, the amount is about 100 mL/mm². In some instances, depositing about 100 mL/mm² of the mixture provides a crosslinked, hydrophilic copolymer that is about 20 μm in thickness.

Conditions suitable to initiate polymerization (i.e., curing) can be selected based on the characteristics of the initiator and the monomers being polymerized, and as so not to degrade the analyte sensing component. In embodiments where the analyte sensing component is an enzyme, the temperature and pH of the method can be selected to preserve the activity of the enzyme. In certain embodiments the initiator is activated with ultraviolet (UV) light. For example, when 2,2-diemthoxy-2-phenylacetophenone is used as an initiator, curing can be performed with UV light. In embodiments where the mixture is formed from the combination of two or more solutions each having an initiator, the initiators can be the same, or in some instances, can be different.

EXAMPLES

Example 1

Immobilization of GOx in a Crosslinked Methacrylate Copolymer

Three solutions (A-C) were prepared:
A) 25 mg/ml glucose oxidase (GOx) in PBS buffer (pH=7.4)
B) 2-hydroxyethyl methacrylate monomer solution containing 1% by weight di(ethylene glycol) dimethacrylate and 1% by weight 2,2-dimethoxy-2-phenylacetophenone.
C) poly(ethylene glycol) methyl ether methacrylate (average Mn 500, Aldrich product #447943) monomer solution containing 1% by weight di(ethylene glycol) dimethacrylate and 1% by weight 2,2-dimethoxy-2-phenylacetophenone.

Two formulations (F2 and F4) were prepared by combining a volume of each solution (A-C) according to the ratios in the following table:

|  | A | B | C |
| --- | --- | --- | --- |
| Formulation F2 | 0.40 | 0.40 | 0.20 |
| Formulation F4 | 0.40 | 0.35 | 0.25 |

The resulting formulations were thoroughly mixed with a vortex shaker. A micro-syringe was used to deposit 100 mL/mm² of each formulation onto a sensor electrode, and the deposited solution was UV-cured for 5 minutes at 365 nm under nitrogen with an EC-500 light exposure chamber (Electro-Lite Corp). The resulting cured crosslinked copolymers each had a thickness of about 20 µm. The sensor made with Formulation F4, used a greater ratio of solution C to solution B than Formulation F2. Thus, the sensor made with Formulation F4 has a greater ratio of poly(ethylene glycol) methyl ether methacrylate-derived units to 2-hydroxyethyl methacrylate-derived units than the sensor made with Formulation F2.

Example 3

Analyte Sensor Performance in a Glucose Solution

The analyte sensors of Formulation F2 and F4 formed in Example 1 were tested at concentrations of glucose in phosphate buffered saline (PBS) ranging from 20 µM to 1000 µm. Both sensors were submerged in PBS and the glucose concentration was increased every 10-15 minutes. The current generated at the electrode was measured using a potentiostat. A linear relationship between current and glucose concentration was observed for both formulations (See inset, FIG. 1). The sensor made with Formulation F4, which was a greater ratio of poly(ethylene glycol) methyl ether methacrylate-derived units to 2-hydroxyethyl methacrylate-derived units than the sensor made with Formulation F2, had a higher current response at the same concentration of glucose than the sensor made with Formulation F2. See FIG. 1.

Although the crosslinked, hydrophilic copolymers in the above examples comprise methacrylate groups, there are a number of ethylenically unsaturated groups known in the art to be capable of undergoing polymerization. Ethylenically unsaturated monomers and macromers may be either acrylic- or vinyl-containing Vinyl-containing monomers contain the vinyl grouping ($CH_2=CH-$), and are generally highly reactive. Acrylic-containing monomers are represented by the formula:

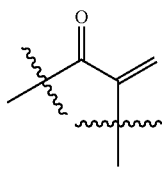 [SMILES: *C(=C)C(*)=O]

Examples of suitable polymerizable groups may include acrylic-, ethacrylic-, itaconic-, styryl-, acrylamido-, methacrylamido- and vinyl-containing groups such as the allyl group.

In addition to the above disclosed methods of forming crosslinked, hydrophilic copolymers by the polymerization of ethylenically unsaturated monomers and macromonomers, additional chemistries will be known to one or ordinary skill in the art to from such copolymers. As an example, epoxy chemistry, in which multifunctional amines and multifunctional epoxy compounds are mixed together and cured, can be used to form crosslinked, hydrophilic copolymers. Additionally, urethane chemistry may be used, in which multifunctional isocyanates are mixed with multifunctional alcohols and cured to provide crosslinked, hydrophilic copolymers. Other chemistries for the formation of crosslinked, hydrophilic copolymers exist, and will be well known to those of ordinary skill in the art.

It should be understood that arrangements described herein are for purposes of example only. As such, those skilled in the art will appreciate that other arrangements and other elements (e.g., machines, interfaces, functions, orders, and groupings of functions, etc.) can be used instead, and some elements can be omitted altogether according to the desired results. Further, many of the elements that are described are functional entities that can be implemented as discrete or distributed components or in conjunction with other components, in any suitable combination and location.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims, along with the full scope of equivalents to which such claims are entitled. It is also to be understood that the terminology used herein is for the purpose of describing particular embodiments only, and is not intended to be limiting.

Further, some embodiments of the system may include privacy controls which may be automatically implemented or controlled by the wearer of the device. For example, where a wearer's collected physiological parameter data and health state data are uploaded to a cloud computing network for trend analysis by a clinician, the data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined.

Additionally or alternatively, wearers of a device may be provided with an opportunity to control whether or how the device collects information about the wearer (e.g., information about a user's medical history, social actions or activities, profession, a user's preferences, or a user's current location), or to control how such information may be used. Thus, the wearer may have control over how information is collected about him or her and used by a clinician or physician or other user of the data. For example, a wearer may elect that data, such as health state and physiological parameters, collected from his or her device may only be used for generating an individual baseline and recommendations in response to collection and comparison of his or her own data and may not be used in generating a population baseline or for use in population correlation studies.

The invention claimed is:
1. An analyte sensor comprising:
a crosslinked, hydrophilic copolymer in contact with a surface of an electrode; and
an analyte sensing component embedded within the crosslinked, hydrophilic copolymer,
wherein the crosslinked, hydrophilic copolymer consists of:
backbone chains comprising;
first methacrylate-derived units, each having a first hydrophilic side chain;
second methacrylate-derived units, each having a second hydrophilic side chain,
wherein the first hydrophilic side chain and the second hydrophilic side chains are the same or different;

third methacrylate-derived units; and
hydrophilic crosslinks between the third methacrylate-derived units in different backbone chains, wherein the hydrophilic crosslinks comprise poly(alkylene oxide).

2. The sensor according to claim 1, wherein the side chain of the first methacrylate-derived units comprise one or more hydroxy groups.

3. The sensor according to claim 1, wherein the first methacrylate-derived units have the structure of formula (Ia):

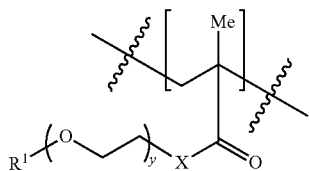

wherein
X is —O—, —NR'— or —S—;
y is 0-10; and
R$^1$ is hydrogen, —C$_1$-C$_{12}$alkyl, —C$_1$-C$_{12}$alkyl-OH, —SiR'$_3$, —C(O)—C$_1$-C$_{12}$alkyl, —C$_1$-C$_{12}$alkyl-C(O)OR', wherein R' is —C$_1$-C$_{12}$alkyl.

4. The sensor according to claim 1, wherein the first methacrylate-derived units have the structure:

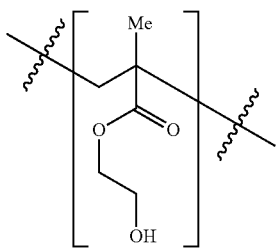

5. The sensor according to claim 1, wherein the second methacrylate-derived units comprise one or more alkylene oxide units.

6. The sensor according to claim 1, wherein the second methacrylate-derived units have the structure of formula (II):

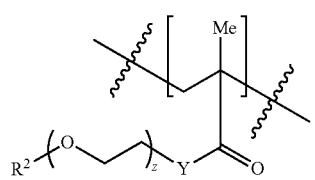

wherein
Y is —O—, —NR'— or —S—;
R$^2$ is hydrogen, —C$_1$-C$_{12}$alkyl, —SiR'$_3$, —C(O)—C$_1$-C$_{12}$alkyl, —C$_1$-C$_{12}$alkyl-C(O)OR', where R' is hydrogen or —C$_1$-C$_{12}$alkyl; and
z is 0-10.

7. The sensor according to claim 1, wherein the second methacrylate-derived units have the structure of formula: (II)

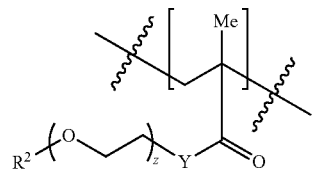

wherein
Y is —O—, —NR'— or —S—;
R$^2$ is hydrogen, —C$_1$-C$_{12}$alkyl, —SiR'$_3$, —C(O)—C$_1$-C$_{12}$alkyl, —C$_1$-C$_{12}$alkyl-C(O)OR', where R' is hydrogen or —C$_1$-C$_{12}$alkyl; and
z is an average value of from 2 to about 250.

8. The sensor according to claim 1, wherein the hydrophilic crosslinks have the structure of formula (IIIa):

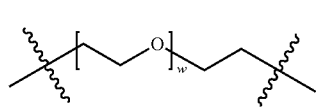

wherein w is 2-10.

9. The sensor according to claim 1, wherein the hydrophilic crosslinks have the structure of formula (IIIa):

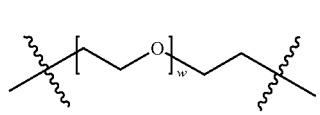

wherein w is an average value of from about 2 to about 250.

10. The sensor according to claim 1, wherein the analyte sensing component comprises glucose oxidase.

11. The sensor according to claim 1, wherein the crosslinked, hydrophilic copolymer has a thickness of about 20 μm.

12. The sensor according to claim 1, wherein
the first methacrylate-derived units are derived from 2-hydroxyethylmethacrylate;
the second methacrylate-derived units have the structure of formula (II):

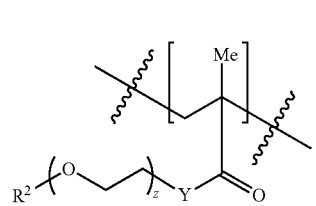

wherein
Y is —O—, —NR'— or —S—;
R$^2$ is hydrogen, —C$_1$-C$_{12}$alkyl, —SiR'$_3$, —C(O)—C$_1$-C$_{12}$alkyl or —C$_1$-C$_{12}$alkyl-C(O)OR', wherein R' is hydrogen or 13 C$_1$-C$_{12}$alkyl; and
z is an average value of from about 10 to about 15;
the hydrophilic crosslinks have the structure of formula (IIIa):

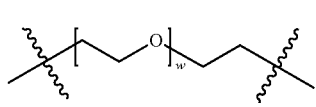 (IIIa)
wherein w is 2; and
the analyte sensing component comprises glucose oxidase.
* * * * *